United States Patent [19]

Freeman et al.

[11] Patent Number: 5,769,831
[45] Date of Patent: Jun. 23, 1998

[54] CONVENIENTLY DISPOSABLE OSTOMY APPLIANCE

[75] Inventors: Harvey Alan Freeman, Sparta, N.J.; David Young Phelps, Anchorage, Ky.

[73] Assignee: Louisville Laboratories, Inc., Louisville, Ky.

[21] Appl. No.: 670,701

[22] Filed: May 25, 1996

[51] Int. Cl.$^6$ ............................................. A61F 5/44
[52] U.S. Cl. ........................ 604/332; 604/342; 604/338
[58] Field of Search .............................. 604/332, 336, 604/338, 339, 342, 344; 128/DIG. 24; 383/109, 111

[56] References Cited

U.S. PATENT DOCUMENTS

| | | | |
|---|---|---|---|
| 4,701,169 | 10/1987 | Steer | 604/344 |
| 5,110,390 | 5/1992 | Martini et al. | 604/338 |
| 5,417,677 | 5/1995 | Schneider et al. | 604/332 |

Primary Examiner—Robert A. Clarke
Attorney, Agent, or Firm—Don Halgren

[57] ABSTRACT

The present invention relates to an ostomy bag having a multi-piece construction with peelable skin surfaces, and multiple perforated layers which are made of dissolvable material. Absorbent material is placed between the layers to facilitate dissolution of the bag when placed in a toilet. The multiple layers of material also permit ready identification to the wearer, by its color change appearance of the inventive applicance, that the layers thereof are properly assembled.

3 Claims, 4 Drawing Sheets

CONVENIENTLY DISPOSABLE OSTOMY APPLIANCE

The invention relates to Ostomy Appliances, and more particularly to appliance construction and methods which permit comfortable use, convenient and environmentally sound disposal.

PRIOR ART

Numerous Ostomy Appliances are known which are intended to simplify the disposal of the waste/fluid collection pouch. A few of the approaches include a pouch that will dissolve (or disperse) in the water of a common toilet bowl and pass through the discharge lines of the waste disposal system.

A flushable Ostomy pouch is shown in U.S. Pat. No. 5,380,309 to Keise, et al., disclosing a pouch with a coupling member which can be removed from the pouch to permit the flush disposal of the envelope without the coupling member. Flushability of this pouch is further facilitated by forming the pouch with converging side walls. None the less, the pouch does not dissolve and the possibility of problems with the bag being deposited in a toilet or septic system remain.

Another flushable Ostomy pouch is shown in U.S. Pat. No. 5,346,482 to Metz, et al., disclosing a flushable two-piece Ostomy appliance system where the pouch can be separated from the patient attachment device prior to flush disposal. This pouch may inadvertently dissolve when exposed to water while being worn. Further, the patient attachment device includes a relatively stiff ring for attachment of the pouch. This relatively stiff ring may not conform to body and skin movements and may be uncomfortable for the wearer.

A further patent showing a flushable ostomy pouch is shown in U.S. Pat. No. 5,417,677 to Schneider, et al., wherein the pouch has side walls composed of pH-sensitive material which is capable of dissolving when exposed to an aqueous fluid, the pouch itself containing pockets of pH-effecting material for dissolution of the pouch when it is dropped in a toilet. This patent, however, requires the wearer of the pouch to also wear a quantity of pH-modifying material. It would be more desirable not to have the wearer of such a pouch subject to the potential danger.

Most current Ostomy pouches, including the device in U.S. Pat. No. 5,380,309, are comprised of materials that do not naturally biodegrade in a sanitary landfill. Both the materials that comprise the pouch and the patient attachment device are nonbiodegradeable in an environmentally sound time frame. Therefore, disposal of such devices in a sanitary landfill will pose a threat to the environment and other ultimate destinations of the soiled product, such as incinerators, are substantially more expensive than landfills.

It is an object of the present invention to overcome the disadvantages of the prior art.

It is yet a further object of the present invention to provide a flushable Ostomy pouch having minimal potential hazards and maximum comfort to the wearer while offering the most environmentally sound, cost efficient and safe means to dispose the soiled pouch. The preferred embodiment that satisfies these requirements includes a dissolvable and flushable pouch that may be safely disposed in a toilet and travel through the discharge lines of the waste disposal system. In order to flush the pouch through the toilet system, the non-dissolvable adhesive components of the patient attachment mechanism must be separated from the dissolvable pouch. Once the pouch is in the final destination of the system, such as a septic tank or municipal solid waste system, the pouch will biodegrade into naturally occuring elements. The materials of the patient attachment component typically do not biodegrade in an environmentally sound time frame. Therefore, this component can be separated from the biodegradeable pouch an disposed in a more environmentally sound fashion.

In the case of a non-flushable Ostomy pouch, it is an object of the current invention to provide a means to separate the biodegradeable components from the non-biodegradeable components for more environmentally acceptable disposal.

In both the flushable and non-flushable embodiments, the object of the current inventions is to provide wearer comfort. This comfort is provided by a low-profile, flexible and conformable patient attachment mechanism. Therefore, the patient attachment mechanism will not excessively protrude from the wearers skin and interfere with clothes and the wearer may flex and bend without obstruction by rigid components of the mechanism.

BRIEF SUMMARY OF THE INVENTION

The present invention comprises a one-piece or two-piece Ostomy Appliance which allows conformance to the skin and body movements and convenient separation of the pouch from the patient attachment component or device with minimal if any nonflushable or nonbiodegradeable components remaining attached to the pouch itself. This feature is useful for pouches which are fabricated from material that is intended to be deposited in typical solid waste recepticles. This feature is especially useful for pouches fabricated from material which will dissolve, disperse, or otherwise lose its structural integrity, when exposed to fluid.

The present invention includes not only means for convenient separation of the pouch from the patient attachment components or device, but, in the case of dissolvable pouches, includes means to expedite the loss of pouch structural integrity when exposed to fluid.

The Ostomy pouch is generally formed to create a cavity for the temporary containment of human waste. The proximal wall is that portion of the pouch which is closest to the wearer of the pouch. The pouch may include a generally circular or square flange attached to one of the walls.

In the case of a flushable pouch, one or both of the proximal and distal walls may be comprised of one or more layers of a material that loses its structural integrity when exposed to fluid, such as polyvinyl alcohol. This material may also be a pH-sensitive flexible plastic Urethane that loses its structural integrity when exposed to a fluid with modified Ph above or below normal levels. In the case where one or both of the side walls is comprised of multiple layers, one or more of the layers may be separated by a layer of highly absorbant material, such as tissue paper.

Whether the layers are separated by a highly absorbant material or not, one or more of the layers may have one or more aperatures disposed on the layer. When the pouch is deposited in a fluid bath, these aperatures will allow the fluid to travel within the layers to increase the surface area of the material exposed to the fluid. If the highly absorbant material is present between the layers, the fluid may be more quickly transported between a larger area between the layers. As the surface area of the material exposed to fluid increases, and is exposed to the material more quickly, the time period required for the material to lose its structural integrity will decrease.

To prohibit the material from undesired exposure to fluid, the aperatures may be covered by a seal, such as a pressure sensitive adhesive strip, or a cover over the entire wall of the pouch. Removal of the adhesive strip or cover would permit fluid to contact the wall of the pouch and/or pass through the aperatures and travel to the inside of the layers.

The proximal or distal wall has an opening therethrough. In the case of a pouch with multiple layers, the opening extends through the layers to the internal cavity. Also, in the case of a pouch with multiple layers, the opening is defined by a heat sealed ring, or an adhesive bond, which comprises and annular bond or weld holding together the multiple layers at the opening. The opening is intended for passage of waste or fluids from the wearer of the pouch into the waste/fluid collection cavity.

In the case when a flange is attached to the pouch, the flange assists with attachment of the pouch to the wearer. The flange is comprised of the same material, or similar materials, as the proximal and/or distal wall of the pouch. The flange is heat sealed or otherwise bonded to the distal or proximal wall. In many cases, the flange has an opening therewithin, which opening is coaxial with an opening in the proximal wall. In this case, the flange is attached to the proximal or distal wall by an annular heat seal, adhesive bond, or otherwise attached about the opening in the proximal or distal wall. The flange may be comprised of one or more layers of material. In the case of a flushable pouch, at least one of the layers may be fabricated from a material that loses its structural integrity when exposed to fluid, such as the material of the pouch walls described above. Further, the flange may include one or more aperatures and one or more layers of the flange may be separated by a highly hydrophilic material, in the same fashion as the pouch walls described above.

In either the flushable or non-flushable arrangement, the pouch and flange, if the flange is included in the construction of the pouch, may be comprised of a biodegradeable material, such as a thermo-plastic urethane.

In the case of a one-piece appliance, the pouch may be held to the wearer by a disc shaped component with an adhesive arranged on the patient side for attachment to the patient, and, on the opposite side, a pattern of adhesive arranged for attachment to the pouch, or the flange on the pouch. The patient side adhesive is covered by a release liner material that can be easily removed. Typically, the adhesive on the patient side is more aggressive than the adhesive disposed on the pouch side of the patient attachment component. In any case, the adhesive on the pouch side of the patient attachment component is designed to allow a releasable bond between the pouch, or pouch flange, and the patient attachment component. In most cases, the patient attachment component has a generally circular opening disposed at a midpoint that is alignable with the opening in the pouch.

In the case of a two-piece appliance system, the patient attachment device may be a discshaped device with adhesive arranged on the patient side that is covered by a removeable release liner material, and, on the opposite side, a pattern of adhesive arranged for attachment to the pouch covered by a removeable release liner material. The adhesive on the pouch side of the patient attachment device is designed to allow a refastenable bond beteen the pouch and the patient attachment device. The pouch of the two-piece appliance system is similar in design and nature as the pouch described above.

In an arrangement of both the one-piece patient attachment component and two-piece patient attachment device, a generally circular or rectangular flange may be bonded or welded to the patient and/or pouch side of the patient attachment device or component. The flange may be a single-sided adhesive, double-sided adhesive, a flexible, or semiflexible non-adhesive material. In the case where the flange is comprised of a flexible non-adhesive material, adhesive for attachment to the patient and/or the pouch would be disposed on the side of the flange that faces the patient and/or the pouch. In the case when the flange material configuration, ie. single-sided or double-sided adhesive, resulted in adhesive facing the patient and/or the pouch, an additional adhesive component may not be necessary.

In some cases of both the one-piece and two-piece configuration, the pouch, or a portion of the pouch, or the flange on the pouch, or a portion of the flange on the pouch, if the flange is included in the construction of the pouch, may have a specially designed component of an adhesive system disposed thereon. In this case, the patient attachment component of the one-piece appliance or the patient attachment device of the two-piece system, will have the mating component of the adhesive system disposed thereon. These two components are designed to adhere the pouch to the skin attachment component or device, but allow a releaseable adhesive bond between the pouch and the patient attachment component of the one-piece system and a refastenable bond between the pouch and the patient attachment device of the two-piece system.

In a further arrangement of the patient attachment component of the one-piece appliance or the patient attachment device of the two-piece appliance system, a flexible cylinder is attached to said patient attachment component or device. The cylinder is comprised of a material, such as a thermoplastic elastomer, that is atraumatic to the skin. The cylinder is placed within the central opening in the patient attachment component or device and the walls of the cylinder extend axially with the opening. When the patient attachment component or device is mated with the opening in the proximal or distal wall of the pouch, the cylinder extends into the corresponding opening in the proximal or distal wall, and, if a flange is attached to said distal or proximal wall, into the opening in the flange that corresponds with the opening in the distal or proximal wall. The cylinder extends axially with the opening in the patient attachment component or device towards the wearer side such that the skin will come into slight contact with end of the cylinder when the patient attachment component or device is applied to the wearer. The cylinder includes an annular flange that extends perpendicularly from the axis of the cylinder. This flange is placed between the layers of the patient attachment component or device such that the cylinder is secured to the patient attachment component or device. The cylinder is intended to prohibit contact between waste/fluid and the adhesive bonds between the layers of the patient attachment component or device and the adhesive bond between the patient attachment component or device and the pouch, and/or the flange on the pouch.

In an arrangement to permit a user of the pouch, either one-piece or two-piece, to easily and accurately determine whether the pouch is properly placed upon the patient attachment component or device, the pouch, or a portion of the pouch, or the flange, or a portion of the flange, if the flange is included in the construction of the pouch, may have a colorant disposed therein or thereon, such as for instance yellow or blue. The patient attachment component or device, or a portion of the patient attachment component or device, may have an alternate yet corresponding color such as yellow or blue. In any case, a color which when combined with the color of the pouch of flange, creates a different third color.

In operation of the one-piece non-flushable Ostomy Appliance of the present invention, the patient removes the release liner material from the adhesives on the patient side of the patient attachment component. The pouch is secured to the patient as the adhesive is applied to the skin. Prior to disposal of the pouch, the appliance is removed from the skin and the pouch is removed from the patient attachment component by breaking the releaseable bond between the adhesives on the patient attachment component and the pouch or pouch flange. The patient attachment component can be immediately disposed without difficulty or inconvenience. The patient attachment component should be disposed in a facility designed for non-biodegradeable materials. The pouch, with remants of the waste material therein, may be compactly packaged without the bulky adhesive of the patient attachment component, and carried to a more appropriate disposal location. As the pouch may be comprised of a biodegradeable material, the pouch can be disposed in a sanitary landfill where it will degrade into naturally occuring elements in an environmentally sound time frame.

In an arrangement when the pouch of the one-piece Ostomy Appliance is fabricated from a material that loses its structural integrity when exposed to fluid, the adhesive of the patient attachment component typically do not lose their structural integrity in the same time frame as the pouch material when exposed to fluid. This arrangement allows removal of the pouch from the patient attachment component. The pouch is then deposited in a bath of fluid, such as a toilet, where it loses its structural integrity and can be safely flushed through the waste discharge lines and into a septic tank or municipal waste water treatment facility.

In an arrangement when the pouch walls or aperatures in the pouch walls and/or pouch flange are covered by an adhesive seal, the adhesive seal is removed to expose the pouch walls or aperatures prior to disposal in the fluid bath. The fluid in the bath then travels within the walls of the pouch and/or the pouch flange. As the fluid travels between the layers, the surface area of the walls which is in contact with fluid increases. As the surface area increases, the pouch material dissolution time decreases.

The dissolution time of the pouch material may be further reduced in an arrangement where a highly hydrophillic material is placed between the layers of the pouch walls and/or flange. The hydrophillic material will absorb and transport the fluid between the pouch walls and or layers of the pouch flange and expedite dissolution.

In an arrangement where the pouch and/or pouch flange material is comprised of a material that loses its structural integrity when exposed to fluid with modified pH, the pH of the flid bath, such as a toilet, may be modified prior to, or after, deposit of the pouch in the fluid bath.

In operation of the two-piece non-flushable Ostomy Appliance system, the patient removes the release liner material from the adhesives on the patient side of the patient attachment device. The patient attachment device is secured to the patient as the adhesive is applied to the skin. The release liner material is removed from the adhesives on the pouch side of the patient attachment device. As the pouch, or pouch flange, is disposed onto the adhesive component of the patient attachment device, the pouch, or pouch flange, is secured to the patient attachment device. Prior to disposal of the pouch, the pouch is removed from the patient attachment device by breaking the refastenable bond between the adhesives on the patient attachment device and the pouch or pouch flange. The patient attachment device can remain on the patient. The pouch, with remants of the waste material therein, may be compactly packaged without the bulky adhesive of the patient attachment component, and carried to a more appropriate disposal location. As the pouch may be comprised of a biodegradeable material, the pouch can be disposed in a sanitary landfill where it will degrade into naturally occuring elements in an environmentally sound time frame.

Another pouch may then be applied to the patient attachment device. In an arrangement where the patient attachment device and the pouch or pouch flange include two different colors, a third color will be come visible when the patient attachment device and the pouch, or pouch flange, come into intimate contact. In any case, another pouch may be secured to the patient attachment device as the pouch, or pouch flange, is disposed onto the adhesive on the patient attachment device.

In an arrangement of the two-piece Ostomy Appliance when the pouch is fabricated from a material that loses its structural integrity when exposed to fluid, the adhesive of the patient attachment device typically do not lose their structural integrity in the same time frame as the pouch material when exposed to fluid. This arrangement allows removal of the pouch from the patient attachment device. The pouch is then deposited in a bath of fluid, such as a toilet, where it loses its structural integrity and can be safely flushed through the waste discharge lines and into a septic tank or municipal waste water treatment facility.

In an arrangement of the flushable two-piece appliance when the pouch walls or aperatures in the pouch walls and/or pouch flange are covered by an adhesive seal, the adhesive seal is removed to expose the pouch walls or aperatures prior to disposal in the fluid bath. The fluid in the bath then travels within the walls of the pouch and/or the pouch flange. As the fluid travels between the layers, the surface area of the walls which is in contact with fluid increases. As the surface area increases, the pouch material dissolution time decreases.

The dissolution time of the pouch material may be further reduced in an arrangement where a highly hydrophillic material is placed between the layers of the pouch walls and/or flange. The hydrophillic material will absorb and transport the fluid between the pouch walls and or layers of the pouch flange and expedite dissolution.

In an arrangement where the pouch and/or pouch flange material is comprised of a material that loses its structural integrity when exposed to fluid with modified pH, the pH of the flid bath, such as a toilet, may be modified prior to, or after, deposit of the pouch in the fluid bath. The pouch can be flushed, or otherwise pass through waste discharge lines within 2–3 minutes of submersion of the pouch in the pH modified fluid.

BRIEF DESCRIPTION OF THE DRAWINGS

The objects and advantages of the present invention will become more apparent when viewed in conjunction with the following drawings, in which.

DESCRIPTION OF THE PREFERRED EMBODIMENTS

Figure 1:
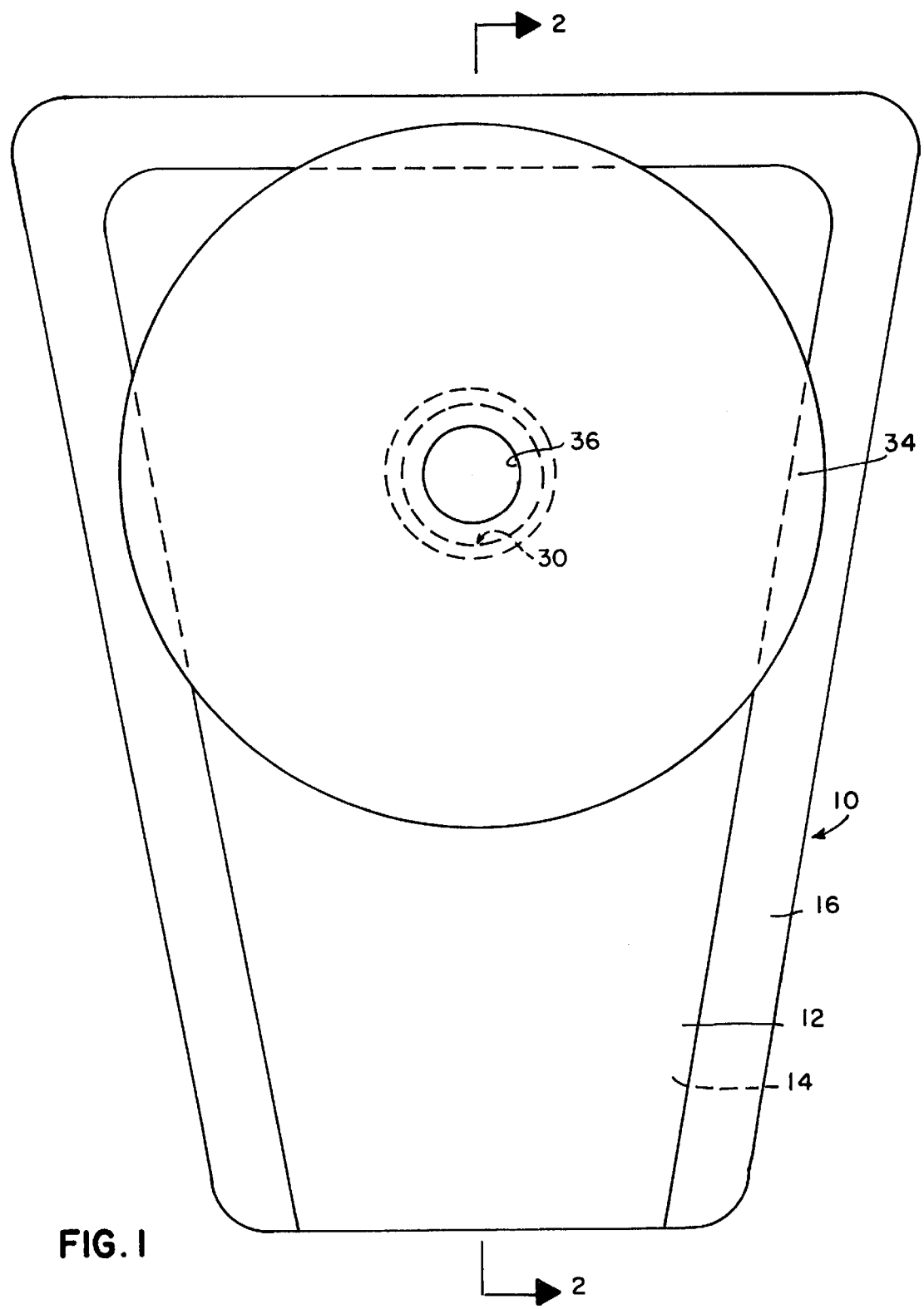
FIG. 1 is a plan view, looking from the pouch wearer's side, of the pouch component of the one-piece appliance or two-piece appliance system.

Referring now to the drawings in detail, and particularly to FIG. 1, there is shown the present invention which comprises a flushable Ostomy appliance 10 which, when exposed to a fluid with a pH above or below a neutral pH level, will dissolve, or lose it's structural integrity. This dissolution is intended to permit disposal of such an ostomy appliance into a toilet bowl, and flushed therewithin.

Figure 2:
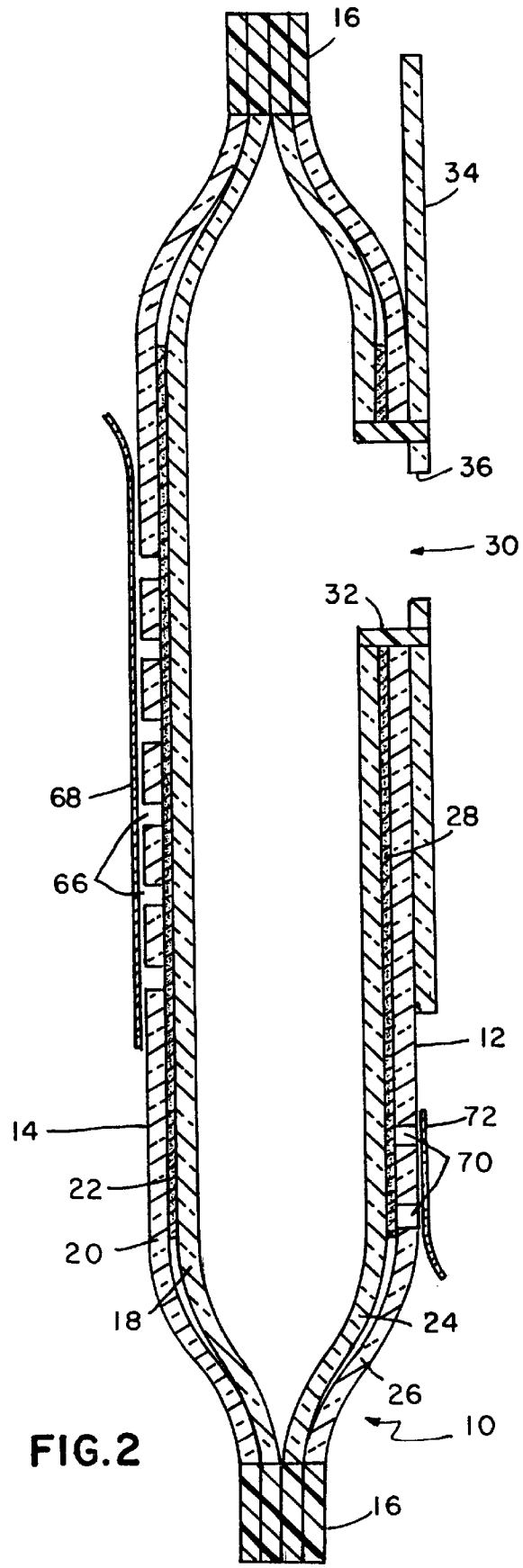
FIG. 2 is a view taken along lines A—A of FIG. 1.

The flushable ostomy appliance 10, otherwise known as a pouch, is generally rectangularly shaped having a flexible proximal and a distal side wall 12 and 14, when folded flat. Although the pouch may be formed from a single cylindrical form, such as blow molding, the preferred embodiment is comprised of two walls which are joined by heat sealing at their periphery 16, to form the pouch for the temporary containment of human waste. The proximal wall 12, as shown in FIGS. 1 and 2, is that portion of the pouch which is closest to the wearer of that pouch. The distal wall 14 is made up of a lamination of a pH sensitive film 18 on its inner layer and a pH sensitive film 20 as an outer layer, each layer 18 and 20 separated by a middle layer 22 having a highly absorbant hydrophillic material therein, such as tissue paper. The pH sensitive films 18 and 20 may be comprised of a flexible thermoplastic urethane.

The proximal wall 12 of the pouch 10, may also have an inner layer 24 of a pH sensitive film, an outer layer 26 of pH sensitive film, and may have a middle layer 28 of highly absorbant hydrophillic material such as tissue paper, similar to that identified as comprising the distal wall 14 of the pouch 10.

The proximal wall 12 has a stomal opening 30 therethrough, adjacent an upper edge thereof. The stomal opening 30 extends through both the inner and outer layers 24 and 26 as well as the middle layer 28 of the proximal wall 12. The stomal opening 30 is defined by a heat sealed ring 32 which comprises an annular weld holding together the inner and outer layers 24 and 26 of the proximal wall 12 together at the opening.

A disc shaped flexible plastic flange 34 is held to the proximal wall 12 of the pouch by the annular heat seal 32. The flange 34 has an opening 36 therewithin, which opening 36 is coaxial with the heat seal 30 in the proximal wall 12. The disc shaped flange is also made of a pH sensitive material which is dissolvable in a toilet bowl which has been treated with a pH modifying material such as ammonia, either in gaseous, tablet, granular or liquid form.

Figure 3:
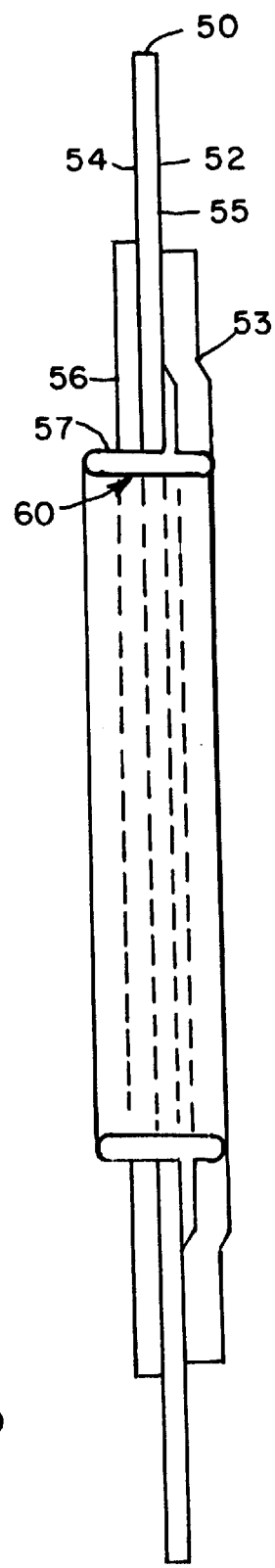
FIG. 3 is a plan view of a skin attachment component or device for the pouch of the present invention.
Figure 4:
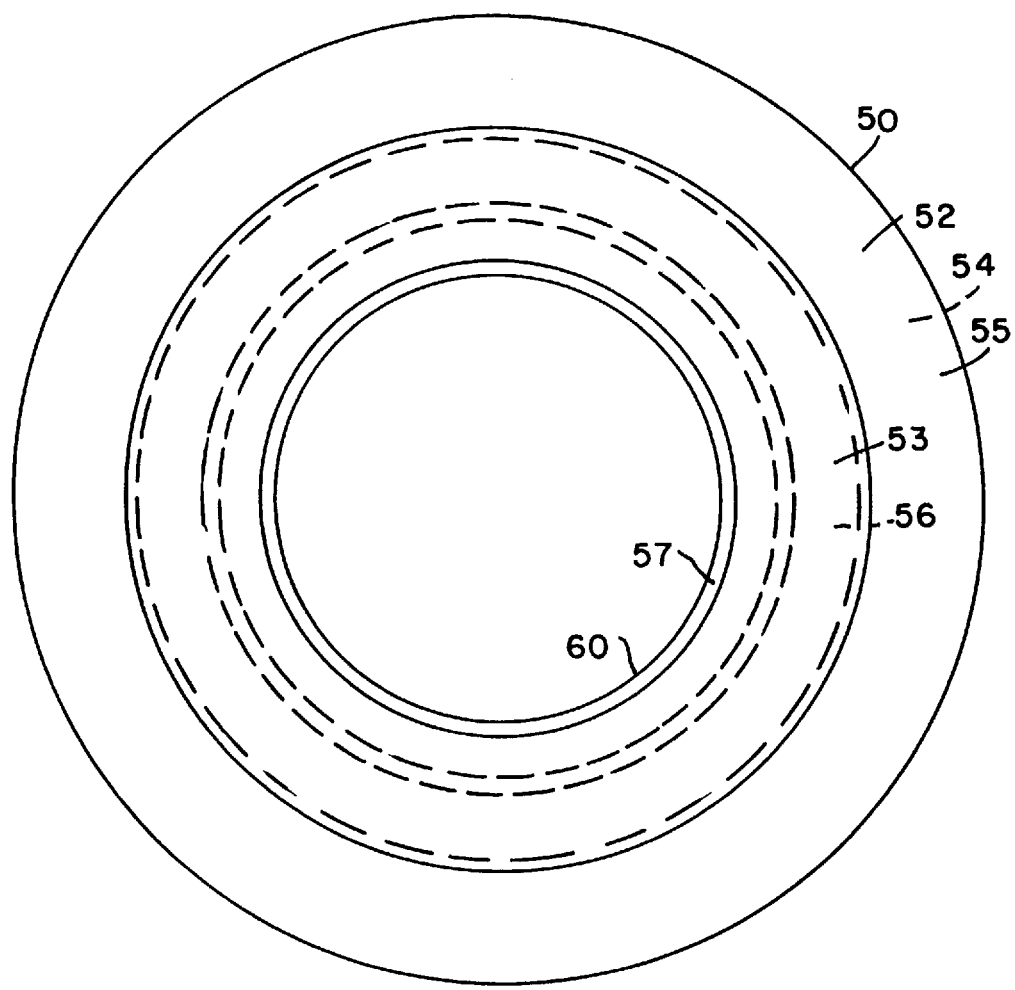
FIG. 4 is a view taken along the lines B—B of FIG. 3

A second component of the ostomy pouch appliance 10 of the present invention, comprises a disc shaped flexible patient attachment device 50, as shown in FIGS. 3 and 4, having a diameter which generally corresponds to the flexible flange 34 attached to the proximal wall 12 of the pouch. The disc shaped patient attachment device 50 has a first or patient side 52 having an outer annular ring of single sided aggressive adhesive 55 thereon. On the opposite side 54 of the disc shaped patient attachment component 50, an annular disc shaped pattern of somewhat less aggressive double sided adhesive 56, such as 3M's acrylate adhesive is disposed thereon. A circular pattern of a mildly aggressive adhesive 53 is arranged on the patient side 52 of the patient attachment component 50. This adhesive is a hydrocolloid material that absorbs fluids and maintains the cleanliness of the skin near the stomal opening of the patient. A central generally circular opening is disposed at a midpoint through the patient attachment component 50 and hydrocolloid adhesive 53. A cylinder with an annular flange which extends perpendicular to the axis of the cylinder 57 is located within the stomal opening 60 of the patient attachment device 50. The annular flange of the cylinder 57 is positioned between the hydrocolloid adhesive 53 and the annular ring of single sided adhesive 55 which secures the cylinder 57 in place. The internal diameter of the cylinder 57 defines the opening for placement of the stoma and passage of waste through the patient attachment component 50 and into the pouch 10 and protects the adhesive bonds between the annular ring of adhesive 55, the hydrocolloid adhesive 53 and the double sided adhesive 56 of the patient attachment component 50 and the adhesive bond between the double sided adhesive 56 of the patient attachment component 50 and the flange 34 of the pouch 10. The external diameter of the cylinder 57 is alignable with the stomal opening 30 of the pouch.

The "pouch side" annular band of adhesive 56 may be comprised of a double sided adhesive with the strength of the pouch side of the double sided adhesive being less aggressive than the annular band of adhesive 55 and the hydrocolloid adhesive 53 facing the patient's skin on the opposed side of the patient attachment component 50.

A plurality of aperatures 66 are disposed on the outer wall 20 of the pH sensitive film which comprises the distal wall 14 of the pouch. A water resistant pressure sensitive adhesive strip 68 may be sealingly disposed over the aperatures 66 in the outer pH sensitive film comprising the distal wall 14. A further plurality of the aperatures 70 may be disposed in the pH sensitive film defining the outer wall 26 surface of the proximal, or patient facing wall 12 of the pouch 10. The aperatures 70 may also be releasably sealed by an adhesive strip 72 thereon. Removal of the adhesive strips 66 and 72 would permit water (from the toilet bowl into which the pouch were dropped) to wick up and penetrate the tissue layers 22 and 28 between the two dissolvable layers of material 18/20 and 24/26 making up the proximal and distal walls 12 and 14 of the pouch 10.

In an arrangement to permit the user of the pouch to easily and accurately determine whether the pouch flange 34 is properly placed upon the double sided adhesive 56 of the patient attachment component 50, the flexible flange 34 on the proximal wall 12 of the pouch 10, may have a colorant disposed therein, such as for instance yellow or blue. The skin barrier 50, to which the flexible flange 34 is attached, may have an alternate yet corresponding color such as blue or yellow, in any case, a color which when combined with a color of the flexible flange 34 creates a different third color when they are mated upon one another, to indicate proper alignment (no one color showing, but their combined color, ie. yellow+blue=green) when the two different colored components (flange 34 and patient attachment component 50) are mated together properly.

In operation of the flushable ostomy appliance of the present invention, the Ostomate or wearer of the pouch simply takes a pH modifying tablet, gas or liquid, such as made from ammonia, and disposes it into a typical toilet bowl. The flushable pouch 10 may then beeasily removed from the patient by peeling the disc shaped flange 34 from the double-sided adhesive 56 of the the patient attachment device 50 adhesively attached to the patient's skin. The patient or Ostomate drops the flushable pouch into the pH modified water within the toilet bowl, after having removed the pressure sensitive adhesive strips 68 and 72 from the aperatures 66 and 70 on both the outerside of the distal wall 14 and the outerside of the proximal wall 12. The pH modified water within the toilet bowl thus flows into the aperatures 66 and 70 on both the distal wall 14 and the proximal wall 12 and is absorbed by the hydrophillic material 22 and 28 between the two layers of pH sensitive films 18/20 and 24/26 defining each wall 14 and 12.

A further embodiment is contemplated without the middle layer of hydrophillic material between the pH sensitive film layers defining each proximal and distal wall. The water from the pH modified toilet bowl travels into the space between the flexible layers of the pH sensitive film 18/20 and 24/26, and begins the dissolution thereof. After an appropriate time, i.e. about 2–3 minutes, the patient may flush the now dissolved pouch down the drain.

Non-Flushable - (1) Piece

We claim:

1. A two-piece waste/fluid collection system, comprising a waste/fluid collection pouch and a patient attachment device, which permits the simple and convenient disposal of said pouch, comprising:

said pouch having a distal wall and a proximal wall joined at their peripheries to define a waste/fluid cavity, with a flange attached to said distal wall;

an opening in said proximal wall to permit passage of waste/fluid into said cavity from a patient wearing said pouch;

said patient attachment device having an adhesive arranged thereon for attachment to both said patient and to said pouch and wherein said flange has a first color, and said attachment component has a second color, which when said components are juxtaposed adjacent to one another, a third resultant color is viewable.

2. The waste/fluid collection system as recited in claim 1, wherein said flange on said pouch has an adhesive system component attached thereto for attachment to said patient attachment component.

3. A two piece waste/fluid collection system, comprising a waste/fluid collection pouch and a patient attachment device, for the simple and convenient disposal thereof, comprising:

a distal wall and a proximal wall joined at their peripheries to define a waste fluid confining cavity an opening in said proximal wall, to permit passage of waste/fluid into said cavity from a patient wearing said pouch;

said patient attachment device having adhesive arranged for attachment to said patient and to said pouch wherein said pouch has a first color, and said attachment component has a second color, which when said pouch and said attachment component are juxtaposed adjacent to each other, a third color is viewable.

* * * * *